United States Patent [19]
Koledin

[11] Patent Number: 5,865,773
[45] Date of Patent: Feb. 2, 1999

[54] CERVICAL EXTRICATION COLLAR

[76] Inventor: Michael J. Koledin, P.O. Box 1414, Cornelius, N.C. 28031

[21] Appl. No.: 15,486

[22] Filed: Jan. 28, 1998

[51] Int. Cl.⁶ ...................................................... A61F 5/00
[52] U.S. Cl. ...................................... 602/18; 128/DIG. 23
[58] Field of Search ................. 602/17–19; 128/DIG. 23

[56] References Cited

U.S. PATENT DOCUMENTS

| | | | |
|---|---|---|---|
| 2,223,276 | 11/1940 | Ward | 602/18 |
| 2,820,455 | 1/1958 | Hall | 602/18 |
| 2,904,040 | 9/1959 | Hale | 602/18 |
| 3,024,784 | 3/1962 | Monfardini | 602/18 |
| 3,042,027 | 7/1962 | Monfardini | 602/18 |
| 3,177,869 | 4/1965 | Bartels | 602/18 |
| 3,220,406 | 11/1965 | Connelly | 602/18 |
| 3,916,885 | 11/1975 | Gaylord, Jr. | 602/18 |
| 4,712,540 | 12/1987 | Tucker et al. . | |
| 4,793,334 | 12/1988 | McGuinness et al. | 602/18 |
| 5,005,563 | 4/1991 | Veale | 602/18 |
| 5,215,517 | 6/1993 | Stevenson et al. | 602/18 |
| 5,366,438 | 11/1994 | Martin, Sr. . | |
| 5,433,696 | 7/1995 | Osti | 602/18 |
| 5,520,619 | 5/1996 | Martin . | |
| 5,593,382 | 1/1997 | Rudy, Jr. et al. . | |
| 5,688,229 | 11/1997 | Bauer | 602/18 |

*Primary Examiner*—Linda C. M. Dvorak
*Attorney, Agent, or Firm*—Bell Seltzer Intellectual Property Law Group of Alston & Bird LLP

[57] ABSTRACT

An emergency extrication collar comprising a flexible band for encircling the wearer's neck, a chin support member which may be readily adjusted in elevation with respect to the band so as to permit adjustment to fit patients having varying neck sizes. The chin support member is connected to the band by a post which is slidably connected to a vertical strap on the band, and such that the elevation of the chin support member above the post, and thus the neck size of the collar, may be adjusted by simply sliding the post and chin support upwardly to any selected size between the size extremes. A pawl and ratchet interconnection between the post and strap precludes movement in the opposite direction. The collar is secured in its adjusted size by a locking arm which is pivotally mounted on the post, and movement of the locking arm to its release position also releases the pawl and ratchet interconnection.

20 Claims, 5 Drawing Sheets

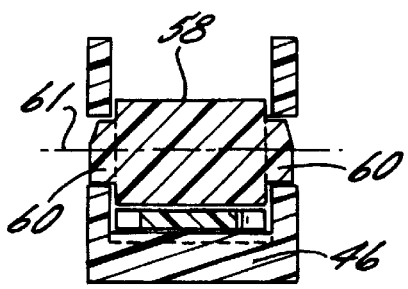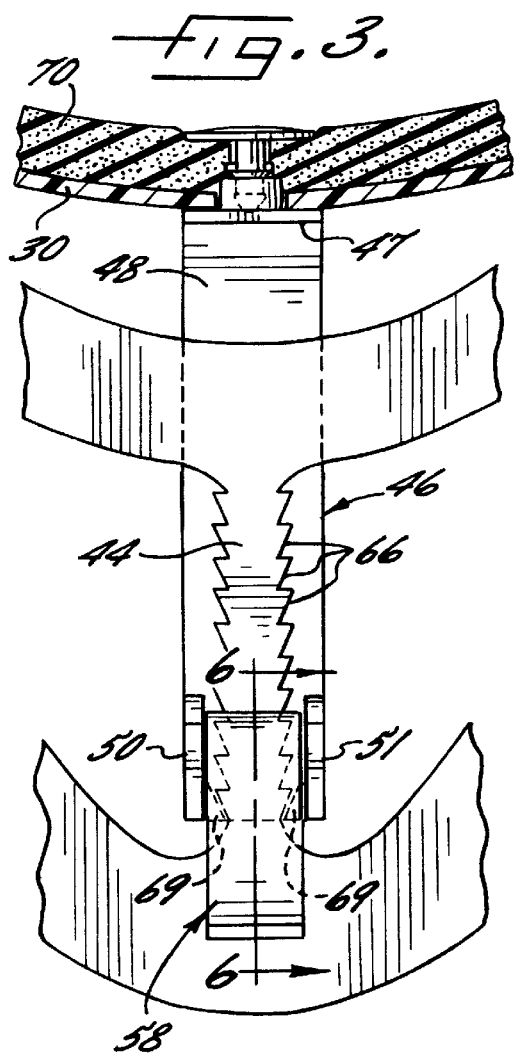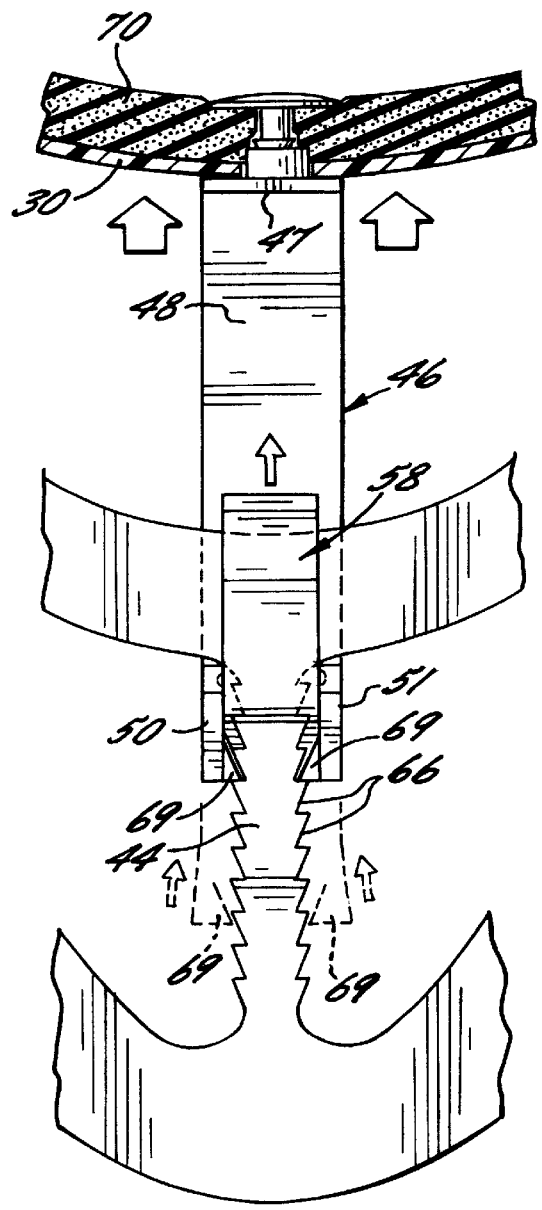

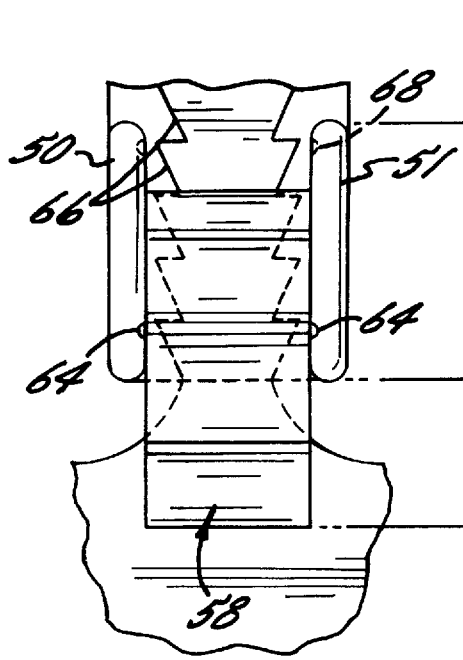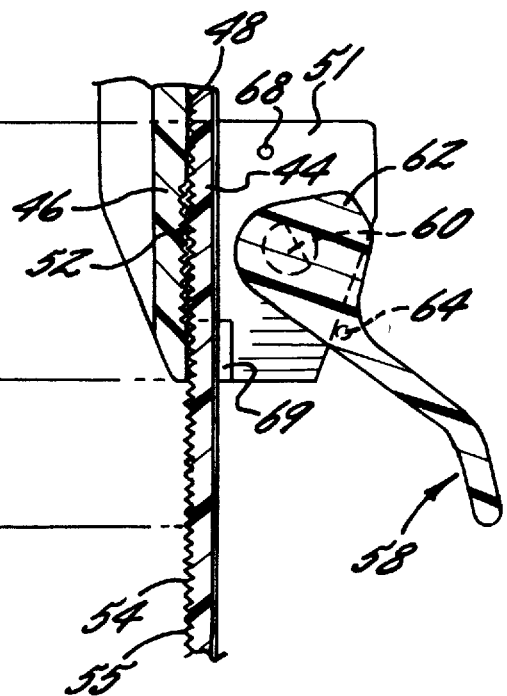
Fig. 8A. Fig. 8B.
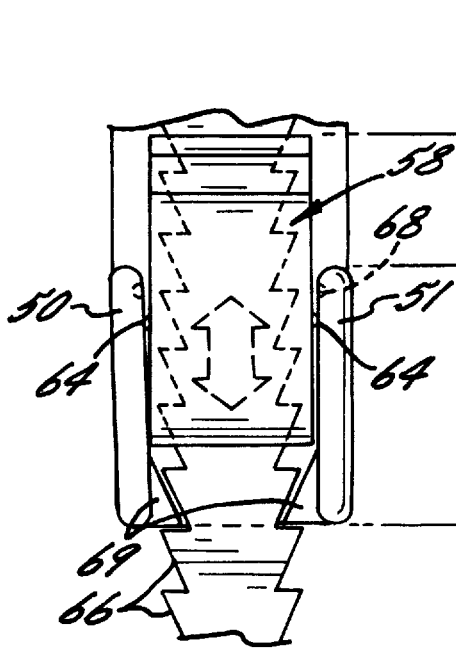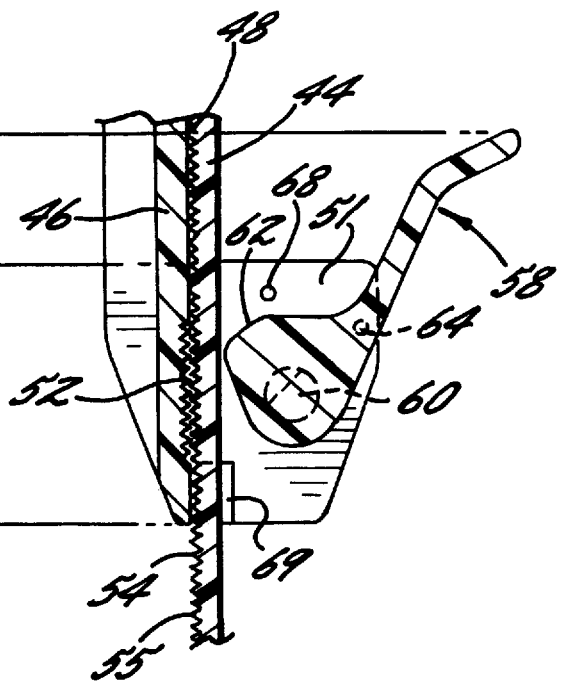
Fig. 9A. Fig. 9B.

CERVICAL EXTRICATION COLLAR

BACKGROUND OF THE INVENTION

The present invention relates to a cervical collar which is adapted to be sized on or off the patient and be efficiently and properly applied to the neck of a patient under emergency or non-emergency conditions.

Cervical collars are commonly used to restrict the movement of the head and neck of a person who has suffered a neck or spinal injury, and such collars are often applied in the field under emergency conditions so as to permit the extrication of an injured person from an accident site while the upper cervical spine is immobilized.

In instances where the collar is to be applied under emergency conditions, it is important that the collar can be easily applied about the neck of the patient, and adjusted in height to fit the neck of the patient, without risk of further injury or trauma. Several prior collar designs have been proposed to achieve these functions, including those disclosed in U.S. Pat. Nos. 5,520,619 and 5,593,382.

It is an object of the present invention to provide an improved cervical collar of the described type, and which can be easily applied to an injured person under emergency conditions, and readily sized to the patient either before or after it has been applied.

It is a more particular object of the present invention to provide a cervical collar which is readily adjustable to the neck size of the patient under emergency conditions and so as to be infinitely adjustable to any position between the shortest and longest neck sizes.

It is also an object of the present invention to provide a cervical collar that provides full and proper support to the patient once it is applied, and which is able to effectively immobilize the upper cervical spine of an injured person.

SUMMARY OF THE INVENTION

The above and other objects and advantages of the present invention are achieved in the embodiment illustrated herein by the provision of a cervical collar which comprises an elongate generally flat band having a sufficient longitudinal length and flexibility to encircle a patient's neck in use, and which includes an upper edge and a lower edge. A chin support member is joined along the upper edge of the band, and the joining structure includes a post which is fixed to the chin support member so as to extend downwardly therefrom. The post and the band are slidably interconnected by a structure which includes a locking arm pivotally mounted to one of the post and the band so as to be manually pivotable between a release position wherein the post is freely slidable relative to the band in either vertical direction to permit upward and downward movement of the chin support member, and a locking position wherein the post and the band are tightly pressed against each other to preclude relative sliding movement between the post and the band. Also, hook and loop fastening strips are mounted to the ends of the band for releasably securing the band in encircling relation about the neck of the patient.

In the preferred embodiment, the structure for slidably interconnecting the post and the band further includes a central opening formed in the band, and a vertical strap formed on the band so as to extend vertically across the opening. The vertical strap overlies the post so that the post is slidable along the strap and the locking arm acts to press the post and the strap together when the arm is pivoted to its locking position.

Also, in the preferred embodiment, the locking arm includes detent means for releasably retaining the locking arm in the locking position. Also, the vertical strap and post may include a pawl and ratchet interconnection which permits sliding movement of the strap and chin support in the upward direction while precluding sliding movement in the opposite direction. The pawl and ratchet interconnection can be released by pivoting the locking arm to the release position, so as to permit movement of the strap in either direction.

BRIEF DESCRIPTION OF THE DRAWINGS

Some of the objects and advantages of the invention having been stated, others will appear as the description proceeds, when taken in conjunction with the accompanying drawings in which:

FIG. 3 is a fragmentary view showing the post adjusted to a lowered position for accommodating young patients or patients with a relatively short neck;

FIG. 4 is a view similar to FIG. 3 with the post adjusted to a raised position for accommodating patients with a longer neck;

FIG. 5 is a sectional view of the locking arm taken along the line 5—5 in FIG. 3;

FIGS. 8A and 8B; 9A and 9B; and 10A and 10B are views similar to FIGS. 7A and 7B, respectively, and showing the locking arm at several positions, ending in its locking position.

DETAILED DESCRIPTION OF THE PREFERRED EMBODIMENT

Figure 1:
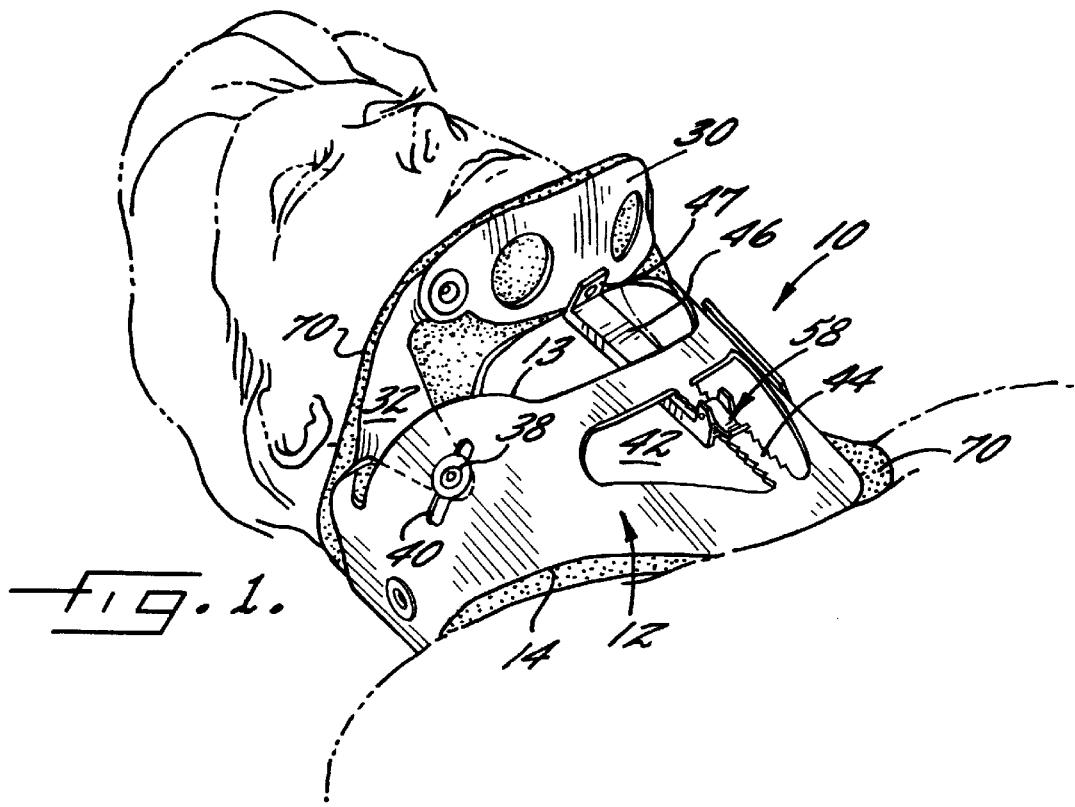
FIG. 1 is a perspective view illustrating a cervical collar which embodies the present invention, applied to a patient.

Referring more particularly to the drawings, an adjustable cervical collar which embodies the present invention is generally indicated at 10 in the drawings.

Figure 2:
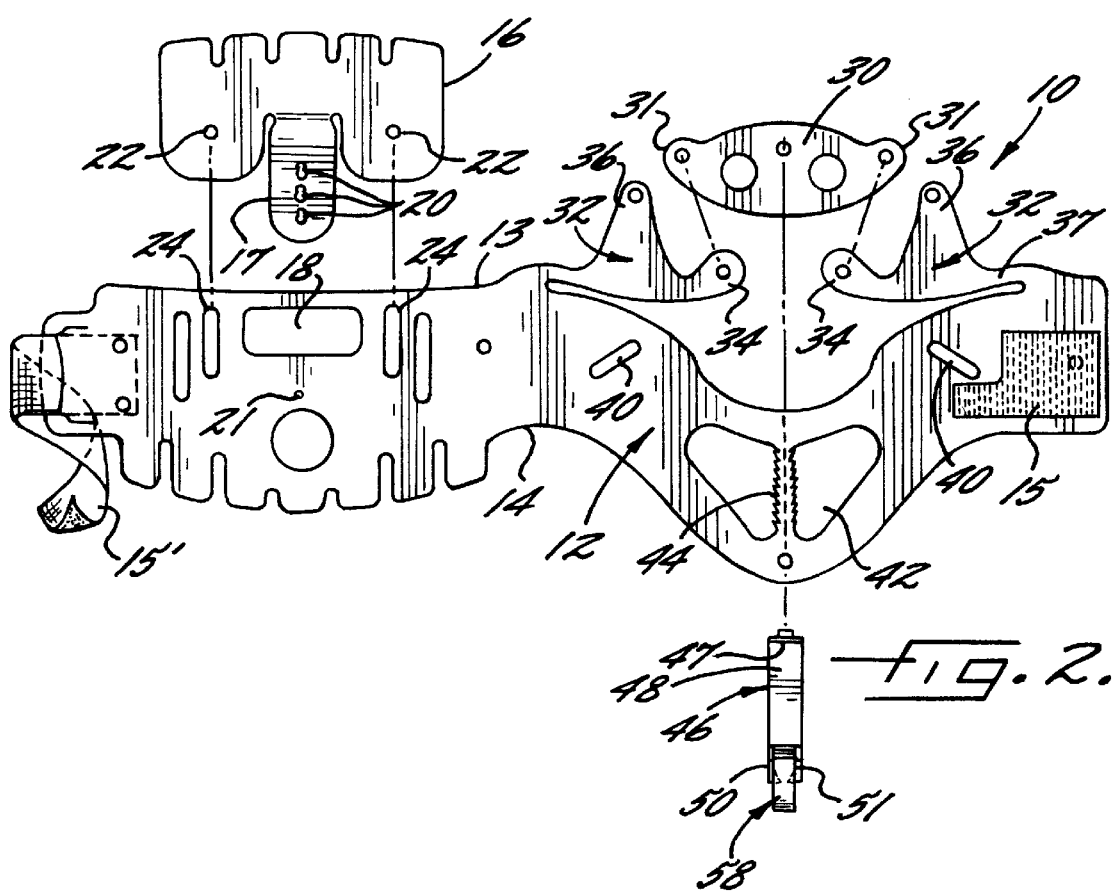
FIG. 2 is an exploded plan view of the band portion of the collar shown in FIG. 1, with the band lying flat.

The collar 10 is composed of a band 12 of flexible plastic sheet material which is normally flat as seen in FIG. 2, and which has a sufficient longitudinal length and flexibility to encircle a patient's neck in use. The band 12 is composed of a suitable plastic, such as high density polyethylene, and it includes an upper edge 13 and a lower edge 14. Also, cooperating hook and loop fastening strips 15, 15' are mounted at respective ends of the band for holding the band in its operative position encircling the neck of the wearer.

The left side portion of the band as seen in FIG. 2 mounts a plastic occipital support 16, which is fabricated from the same plastic sheet material as the band. In the illustrated embodiment, the support 16 is vertically adjustable with respect to the upper edge 13 of the band 12. More particularly, the support 16 includes a depending tab 17 which is received through an opening 18 in the band, and the tab 17 includes three small openings 20 for selectively receiving a pin 21 which is fixed to the band below the opening 18. The openings 20 are slotted as illustrated, and the pin 21 has a T-shaped cross section (not shown) which is configured to be received in any one of the openings 20 so as to lock in the opening when the support 16 is slid downwardly. Also, the support 16 includes two rivets 22, which are slidably received in respective vertical slots 24 in the band. Thus the occipital support 16 may be adjusted vertically between three positions so as to properly fit the neck of the patient, with the pin 21 received in a selected one of the three openings 20.

The right hand portion of the band as seen in FIG. 2 mounts a chin support member 30 along the upper edge 13 of the band 12. More particularly, the chin support member 30 is fabricated from the same plastic sheet material as the band, and the chin support member 30 includes opposite ends 31 which are attached by rivets or the like to respective support arms 32. The support arms 32 are integrally formed with the remainder of the band 12, and are initially configured as seen in FIG. 2. Specifically, each support arm 32 includes an inwardly directed tab 34 which is connected to the chin support member by a rivet as described above, and a second tab 36 which is initially upwardly directed. Also, a narrow strand 37 integrally connects each support member 32 to the remainder of the band 12.

During assembly of the chin support member 30 to the support arms 32, the support arms are rotated 180° at the narrow strands 37, as seen in FIG. 1, causing the tabs 36 to point downwardly. Each tab 36 includes a pin 38 (FIG. 6), which is then slidably received in an inclined slot 40 in the band 12. Thus as the chin support member 30 is moved upwardly or downwardly in the manner further described below, the pins 38 slide upwardly or downwardly in the slots 40, and thereby stabilize the movement of the chin support member.

Figure 6:
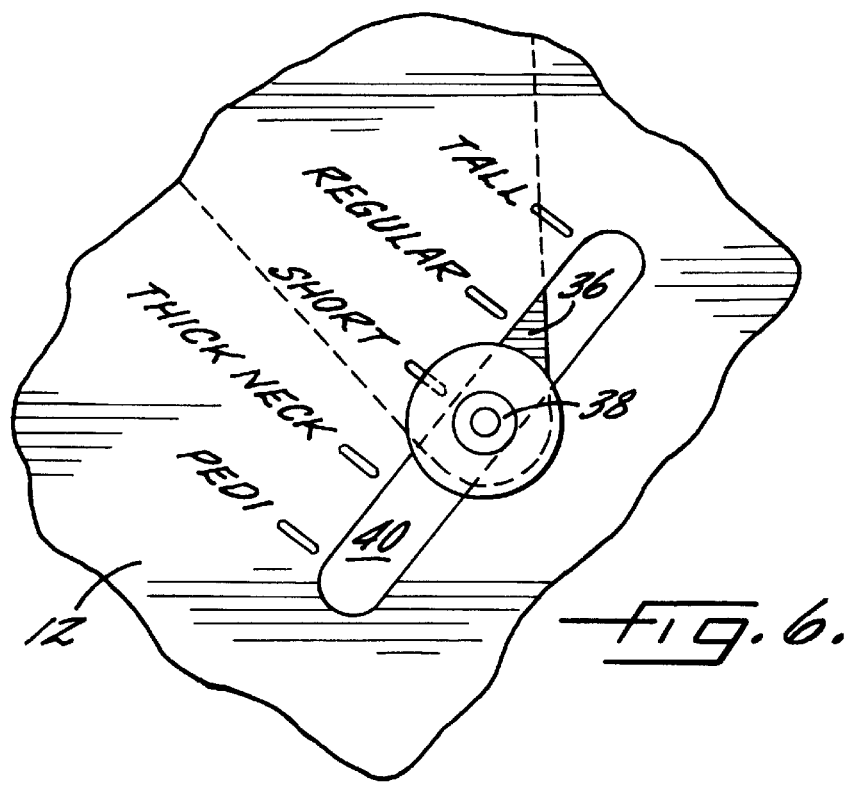
FIG. 6 is a fragmentary view of a portion of the collar which includes one of the slots which slidably supports a support arm for the chin support member.

As best seen in FIG. 6, one or both of the slots 40 may include printed indicia to indicate the vertical spacing of the chin support member from the band, and so as to visually indicate the adjusted size of the collar. As illustrated, five sizes are indicated, ranging from pediatric to tall. If desired, a notch (not shown) may be positioned in the edge of the slot 40 adjacent each indicated size, so as to releasably catch and retain the pin 38 at each size.

The central or medial portion of the chin support member 30 is adjustably connected to the band 12 by a structure which includes a central opening 42 formed in the band 12, and a vertical strap 44 integrally formed on the band so as to extend vertically across the opening 42. A post 46 is joined to an edge portion of the chin support member 30 by a rivet or the like, so as to extend downwardly therefrom, and the lower end of the post 46 is slidably connected to the strap 44 for vertical adjustment therealong, and such that the vertical height of the chin support member 30 may be adjusted.

The post 46 comprises an elongate member which may be composed of a rigid, plastic material, such as injection molded nylon, and its upper end includes a flange 47 which is riveted to the edge of the chin support member. This connection in turn holds the support arms 32 so as to be rotated by 180° at the narrow strands 37 as described above, and the chin support member 30 forms a generally horizontal platform for supporting the chin of the wearer.

The post 46 includes a generally flat outer surface 48, and the lower end of the post includes a pair of longitudinally spaced apart wings 50, 51 which extend upwardly from the outer surface 48 and receive the strap 44 therebetween. The portion of the outer surface 48 between the wings includes transverse serrations 52 (note FIG. 10C), for the purpose described below. The strap 44 includes a generally flat lower or inner surface 54 which directly overlies the outer surface 48 of the post 46, so that the post is freely slidable along the strap in either direction to permit upward and downward movement of the chin support member 30. The lower or inner surface 54 includes transverse serrations 55 along substantially its entire length.

The post 46 may be locked in any selected position along the length of the strap, and for this purpose, there is provided a locking arm 58 which is pivotally mounted between the wings 50, 51 at the lower end of the post 46. More particularly, and as best seen in FIG. 5, the locking arm 58 includes an integral axle 60 which is received in cooperating openings of the wings 50, 51 to define a longitudinal pivot axis 61. Also, the locking arm 58 includes a radially extended head 62, and a pair of aligned detents 64 on its opposite side edges, for the purposes described below.

The locking arm 58 may be pivoted to a release position (FIGS. 7A and 7B) wherein the head 62 and all portions of the locking arm are spaced from the outer surface 48 of the post 46 a distance greater than the thickness of the strap 44, and so that the post is freely slidable in either direction along the strap. In the release position, it will be noted that the detents 64 are in engagement with the wings 50, 51 and have laterally spread the wings apart, note FIG. 7A.

Figures 7A, 7B:
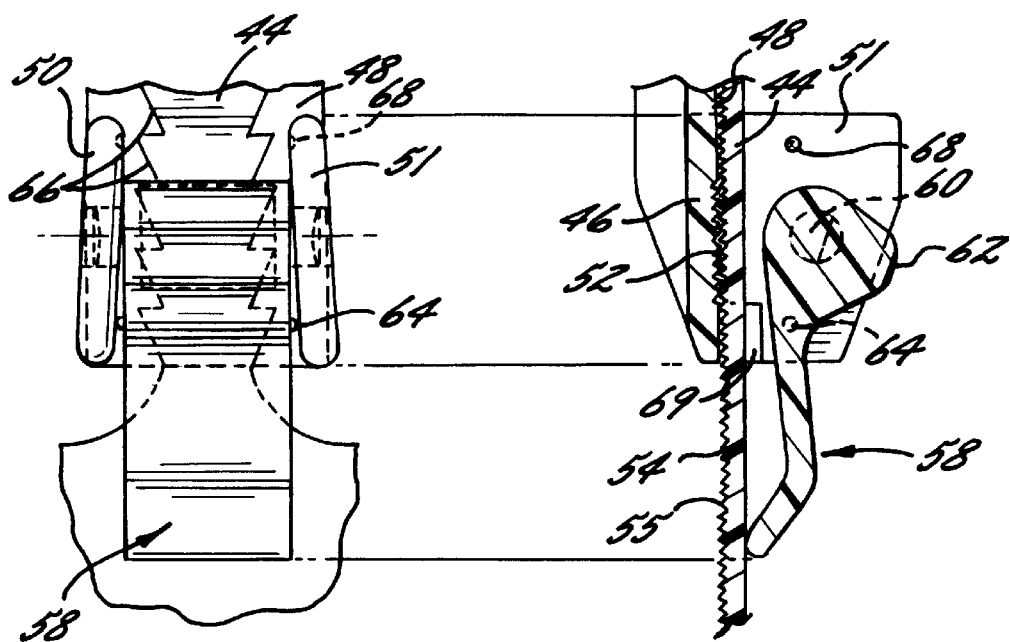
FIGS. 7A and 7B are fragmentary top plan and sectioned side elevation views respectively, showing the locking arm in its released position.
Figures 10A, 10B:
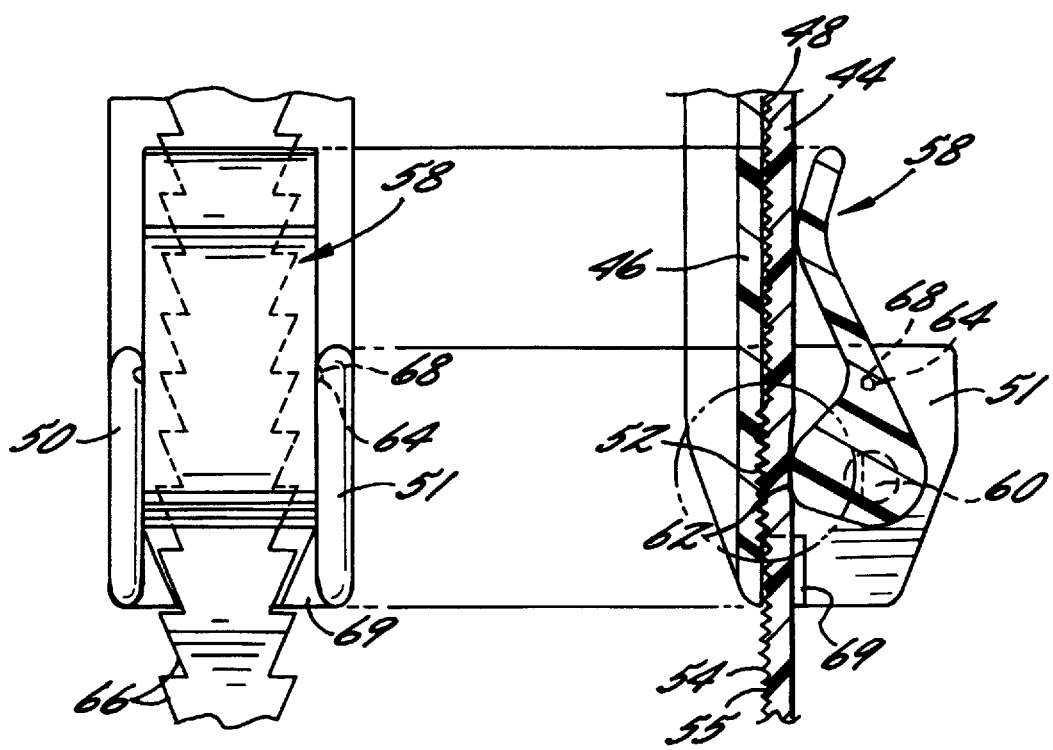
FIG. 10C is an enlarged detail view showing the interengagement of the serrations on the post and strap when the locking arm is in its locking position.
Figure 10C:
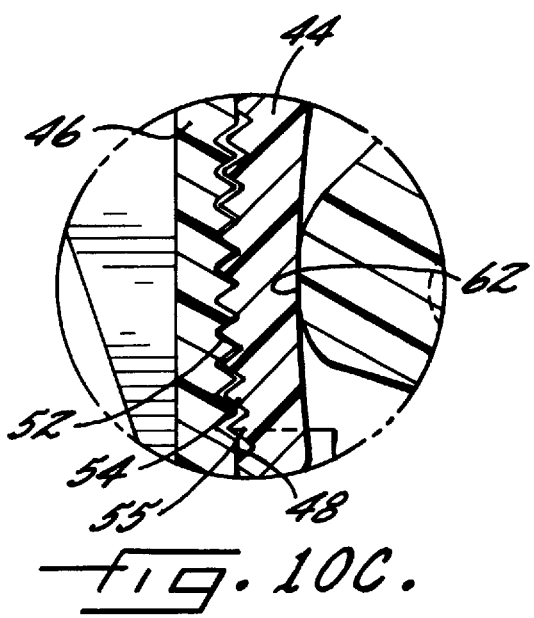

Upon rotation of the locking arm 58 counterclockwise from the release position as seen in FIG. 7B, the detents 64 are removed from between the wings 50, 51 as seen in FIGS. 8A and 8B, and with continued rotation, the detents 64 again enter between and expand the wings and the head 62 is brought into contact with the strap 44 so as to press the strap into firm engagement with the post 46. Thus the serrations 52 on the post 46 interengage with the serrations 55 on the strap 44. This constitutes the locking position as seen in FIGS. 10A and 10B, wherein the post is locked with respect to the strap, with the serrations 52 and 55 firmly interengaged. Also, upon reaching the locking position, the detents 64 snap into receptacles 68 formed in the inner side walls of the wings 50, 51, so as to effectively lock the locking arm 58 in the locking position. In order to release the locking arm, it is necessary to pivot the locking arm clockwise with sufficient force to move the detents 64 out of the receptacles 68 and laterally flex the wings.

In the illustrated embodiment, a pawl and ratchet interconnection is also provided between the post 46 and strap 44, which permits sliding movement of the post only in the upward direction while precluding sliding movement in the opposite direction. The pawl and ratchet interconnection includes ratchet teeth 66 formed along each of the opposite side edges of the strap 44, and a pawl 69 mounted on the inner side wall of each of the wings 50, 51 for normally engaging the ratchet teeth 66.

The ratchet teeth 66 are of saw tooth configuration, and include inclined edges and transverse edges. The pawls 69 are of similar but oppositely oriented configuration, so that upon upward sliding movement of the post along the strap, the inclined edges of the teeth and pawls engage each other and cause the wings 50, 51 to flex outwardly, note FIG. 4, thereby permitting the desired upward movement. Reverse movement is precluded however, by reason of the interengagement of the transverse edges of the ratchet teeth and pawls.

The pawl and ratchet interconnection is released when the locking arm 58 moves to the release position (FIGS. 7A and 7B) by reason of the fact that the detents 64 move between and spread apart the wings 50, 51. The resulting outward flexure of the wings is sufficient to separate the pawls 69 from the teeth 66, thereby permitting free sliding movement of the post in either direction.

As is conventional, the under surface of the band 12, the occipital support 16, and the chin support member 30 may be covered with a layer 70 of a suitable foam material, so as to improve the comfort of the collar.

In use, the occipital support 16 is initially adjusted to the size of the patient, and the collar 10 is applied to encircle the patient's neck, with the chin support member 30 initially positioned at less height than is expected to be employed. The hook and loop fastening strips 15, 15' are then interconnected to secure the collar in position about the neck, and with the locking arm 58 in its release position, the chin support member 30 is elevated so as to engage the wearer's chin. Concurrently, the pins 38 freely slide upwardly in the slots 40, and the post 46 slides upwardly with respect to the strap 44. Alternatively, the locking arm 58 may be rotated to an intermediate position (FIGS. 8A and 8B) which causes the pawl and ratchet interconnection to become operative and permit only upward movement of the chin support member. When the proper elevation is reached, the locking arm 58 is rotated to its locking position (FIG. 10A and 10B) to complete the assembly procedure. To remove the collar, the locking arm 58 is rotated to the release position, and the procedure is reversed.

As will be apparent, the construction of the interconnection between the chin support member 30 and the band 12 in accordance with the present invention permits the chin support member to be infinitely adjustable between the pediatric and tall positions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A cervical collar adapted for being sized on or off the patient and being efficiently and properly applied to the neck of a patient under emergency or non-emergency conditions, and comprising an elongate generally flat band having a sufficient longitudinal length and flexibility to encircle a patient's neck in use, and including an upper edge and a lower edge and so as to define a vertical direction extending between the upper edge and the lower edge, a chin support member, means joining the chin support member along the upper edge of said band, and comprising a post fixed to said chin support member so as to extend downwardly therefrom, and means slidably interconnecting the post and the band so as to permit relative sliding movement in either vertical direction and which includes a locking arm pivotally mounted to one of the post and the band so as to be manually pivotable between a release position wherein the post is freely slidable relative to the band in either vertical direction to permit upward and downward movement of the chin support member, and a locking position wherein the post and the band are tightly pressed against each other to preclude relative sliding movement between the post and the band, and fastening means mounted to said band for releasably securing said band in encircling relation about the neck of a patient.

2. The cervical collar as defined in claim 1 wherein said post includes an outer surface and said band includes an inner surface which directly overlies said outer surface, and wherein at least one of said outer and inner surfaces includes irregularities for increasing the interengagement between the outer and inner surfaces when said locking arm is in said locking position.

3. The cervical collar as defined in claim 1 wherein said chin support member includes a medial location which is adapted to be located centrally below the patient's chin in use, and wherein said post is aligned along a vertical line which extends through said medial location.

4. The cervical collar as defined in claim 3 wherein said joining means further comprises a support arm joined to the chin support member on each side of said medial location thereof, and means interconnecting each of said support arms to said band.

5. The cervical collar as defined in claim 4 wherein said means interconnecting each of said support arms to said band includes a slot in one of said support arm and said band which is inclined with respect to the longitudinal direction of the band and a pin mounted to the other of said support arm and said band and slidably received in the slot.

6. The cervical collar as defined in claim 5 wherein said means interconnecting each of said support arms to said band further comprises a narrow strand connected between the support arm and the band.

7. The cervical collar as defined in claim 6 wherein each narrow strand is integrally connected between the associated support arm and the band, and is twisted by approximately 180 degrees.

8. A cervical collar adapted for being sized on or off the patient and being efficiently and properly applied to the neck of a patient under emergency or non-emergency conditions, and comprising an elongate generally flat band having a sufficient longitudinal length and flexibility to encircle a patient's neck in use, and including an upper edge and a lower edge and so as to define a vertical direction extending between the upper edge and the lower edge, a chin support member, means joining the chin support member along the upper edge of said band, and comprising (a) a central opening formed in said band, (b) a vertical strap formed on said band so as to extend vertically across said opening, and with said strap including a generally flat inner surface, (c) a post fixed to said chin support member so as to extend downwardly therefrom, and with said post including an generally flat outer surface and a pair of longitudinally spaced apart wings extending upwardly from said outer surface, and (d) means interconnecting the post and the strap with said inner surface of said strap overlying said outer surface of said post and with said strap lying between said wings of said post, and so as to permit relative vertical sliding movement between the post and the strap, said interconnecting means including a locking arm pivotally mounted between said wings so as to overlie the strap and so as to be pivotable about a longitudinal pivot axis between a release position wherein the post is freely slidable along said strap to permit upward and downward adjustment of the chin support member, and a locking position wherein said strap is tightly pressed against the post to preclude relative sliding movement between the post and the strap, and fastening means mounted to said band for releasably securing said band in encircling relation about the neck of a patient.

9. The cervical collar as defined in claim 8 wherein said locking arm includes a shoulder extending radially outwardly from the pivot axis and which is configured to be spaced from the strap when the pivot arm is pivoted to the release position to thereby permit free sliding movement between the post and the strap, and to tightly press the strap against the post when the locking arm is pivoted to the locking position to preclude relative sliding movement between the post and strap.

10. The cervical collar as defined in claim 9 wherein the locking arm includes detent means for releasably retaining the locking arm in the locking position.

11. The cervical collar as defined in claim 9 wherein said interconnecting means further includes a pawl and ratchet interconnection between said post and strap which permits sliding movement of the strap in the upward direction while precluding sliding movement in the opposite direction, and means for selectively releasing the pawl and ratchet interconnection so as to permit movement of the strap in either direction.

12. The cervical collar as defined in claim 11 wherein said strap includes opposite side edges, and wherein said pawl and ratchet interconnection includes ratchet teeth formed along at least one of the side edges of the strap, and at least one pawl mounted on at least one of said wings for normally engaging said ratchet teeth, and wherein the ratchet teeth and the pawl are configured to cause the one wing to laterally flex and thereby permit the ratchet teeth to move past the pawl during upward sliding movement of the strap.

13. The cervical collar as defined in claim 12 wherein said means for selectively releasing the pawl and ratchet interconnection includes said detent means of said locking arm which acts to engage and spread apart said wings when the locking arm is moved to said release position to separate the pawl from the ratchet teeth.

14. The cervical collar as defined in claim 13 wherein at least one of said outer and inner surfaces includes irregularities for increasing the interengagement between the outer and inner surfaces when said locking arm is in said locking position.

15. The cervical collar as defined in claim 8 wherein said chin support member includes a medial location at which said post is joined thereto, and wherein said joining means further comprises a support arm joined to the chin support member on each side of said medial location thereof, and means interconnecting each of said support arms to said band.

16. The cervical collar as defined in claim 15 wherein said means interconnecting each of said support arms to said band includes a slot in one of said support arm and said band which is inclined with respect to the longitudinal direction of the band and a pin mounted to the other of said support arm and said band and slidably received in the slot.

17. The cervical collar as defined in claim 16 wherein said means interconnecting each of said support arms to said band further comprises a narrow strand connected between the support arm and the band.

18. The cervical collar as defined in claim 17 wherein each narrow strand is integrally connected between the associated support arm and the band, and is twisted by approximately 180 degrees.

19. A cervical collar adapted for being sized on or off the patient and being efficiently and properly applied to the neck of a patient under emergency or non-emergency conditions, and comprising an elongate generally flat band having a sufficient longitudinal length and flexibility to encircle a patient's neck in use, and including an upper edge and a lower edge and so as to define a vertical direction extending between the upper edge and the lower edge, a chin support member, means joining the chin support member along the upper edge of said band, and comprising (a) a central opening formed in said band, (b) a vertical strap formed on said band so as to extend vertically across said opening, (c) a post fixed to said chin support member so as to extend downwardly therefrom, and (d) means slidably interconnecting the post and the strap and which includes a pawl and ratchet interconnection between the post and the strap which permits sliding movement of the post in the upward vertical direction while precluding sliding movement in the opposite direction, and means for selectively releasing the pawl and ratchet interconnection so as to permit slidable movement of the post along the strap in either direction, and fastening means mounted to said band for releasably securing said band in encircling relation about the neck of a patient.

20. The cervical collar as defined in claim 19 wherein said pawl and ratchet interconnection includes ratchet teeth mounted to one of the post and the strap and at least one pawl mounted to the other of the post and the strap, and wherein said means for selectively releasing the pawl and ratchet interconnection includes a locking arm pivotally mounted to one of the post and the strap so as to be manually pivotable between a release position wherein the pawl is separated from the ratchet teeth and a locking position wherein the pawl engages the ratchet teeth.

* * * * *